United States Patent [19]
Haimes et al.

[11] Patent Number: 6,022,862
[45] Date of Patent: *Feb. 8, 2000

[54] USE OF PSEUDOPTEROSINS FOR PROMOTING WOUND HEALING

[75] Inventors: Howard B. Haimes, South Natick, Mass.; Pablo A. Jimenez, Ellicott City, Md.

[73] Assignee: VimRx Pharmaceuticals, Inc., Wilmington, Del.

[ * ] Notice: This patent is subject to a terminal disclaimer.

[21] Appl. No.: 08/973,126

[22] PCT Filed: Jun. 6, 1996

[86] PCT No.: PCT/US96/09039

§ 371 Date: Dec. 3, 1997

§ 102(e) Date: Dec. 3, 1997

[87] PCT Pub. No.: WO96/40160

PCT Pub. Date: Dec. 19, 1996

Related U.S. Application Data

[63] Continuation of application No. 08/486,359, Jun. 7, 1995, Pat. No. 5,597,808.

[51] Int. Cl.⁷ .................................................. A61K 31/70
[52] U.S. Cl. ............................................. 514/33; 536/18.1
[58] Field of Search ............................... 514/33; 536/18.1

[56] References Cited

U.S. PATENT DOCUMENTS

| | | | |
|---|---|---|---|
| 4,745,104 | 5/1988 | Jacobs et al. | 514/33 |
| 4,849,410 | 7/1989 | Jacobs et al. | 514/33 |
| 5,597,808 | 1/1997 | Haimes et al. | 514/33 |

OTHER PUBLICATIONS

Look, S.A., et al., "The Pseudopterosins: Anti–inflammatory and Analgesic Natural Products from the Sea Whip *Pseudopterogorgia Elisabethae*," *Proc. Natl. Acad. Sci. USA*, 83:6238–6240 (Sep. 1986).

Look, S.A. and Fenical, W., "The Seco–Pseudopterosins, New Anti–inflammatory Diterpene–Glycosides from a Caribbean Gorgonian Octocoral of the Genus Pseudopterogorgia," *Tetrahedron*, 43(15):3363–3370 (1987).

Roussis, V., et al., "New Antiinflammatory Pseudopterosins from the Marine Octocoral *Pseudopterogorgia Elisabethae*," *J. Org. Chem.*, 55:4916–4922 (1990).

Look, S.A., et al., "The Pseudopterosins: A New Class of Antiinflammatory and Analgesic Diterpene Pentosides from the Marine Sea Whip *Pseudopterogorgia Elisabethae* (Octocorallia)," *J. Org. Chem.*, 51(26):5140–5145 (1986).

Bohlin, L., "Pharmacologically Active Compounds from Marine Organisms," *Acta Pharmaceutical Nordica*, 1(3):175–182 (1989).

Scheuer, P. J., "Marine Natural Products and Biomedicine," *Medicinal Research Reviews*, 9(4):535–545 (1989).

*Primary Examiner*—Elli Peselev
*Attorney, Agent, or Firm*—Hamilton, Brook, Smith & Reynolds, P.C.

[57] ABSTRACT

Methods of promoting would healing and the growth and proliferation of keratinocytes, fibroblasts and endothelial cells are disclosed. These methods comprise contacting a wound with an effective wound healing amount of a composition comprising a pseudopterosin or pseudopterosin derivative.

26 Claims, 1 Drawing Sheet

USE OF PSEUDOPTEROSINS FOR PROMOTING WOUND HEALING

RELATED APPLICATIONS

This application is a 371 of PCT/US96/09039, filed Jun. 6, 1996 which is a Continuation-in-Part of U.S. patent application Ser. No. 08/486,359, filed on Jun. 7, 1995, now U.S. Pat. No. 5,597,808 the entire teachings of which are hereby incorporated into this application by reference.

BACKGROUND OF THE INVENTION

Complications are a constant risk with wounds that have not fully healed and remain open. Although most wounds heal quickly without treatment, some types of wounds resist healing. Wounds which cover large surface areas also remain open for extended periods of time. Consequently, it would be advantageous to accelerate the wound healing process. However, present methods of promoting wound healing are inadequate.

Full and partial thickness burns are an example of a wound type which often covers large surface areas and therefore requires prolonged periods of time to heal. As a result, life-threatening complications such as infection and loss of bodily fluids often arise. In addition, healing in burns is often disorderly, resulting in scarring and disfigurement. In some cases wound contraction due to excessive collagen deposition results in reduced mobility of muscles in the vicinity of the wound. Therefore, there is a continued need to accelerate the rate of healing of the burns and to promote healing processes that result in more desirable cosmetic outcomes and less wound contraction and scarring.

Severe burns which cover large areas are often treated by skin autografts taken from undamaged areas of the patient's body. However, skin grafts suffer from low take rates and therefore often provide only short-term coverage of burns. Consequently, there is also a need for new methods which improve the acceptance rate of skin autografts.

Dermal ulcers are an example of wounds that resist healing. Consequently, dermal ulcers often become chronic wounds. For example, one in seven individuals with diabetes develop dermal ulcers on their extremities, which are susceptible to infection. Individuals with infected diabetic ulcers often require hospitalization, intensive services, expensive antibiotics, and, in some cases, amputation. Dermal ulcers, such as those resulting from venous disease (venous stasis ulcers), excessive pressure (decubitus ulcers) and arterial ulcers also resist healing. The current treatments are limited to keeping the wound protected, free of infection and, in some cases, to restore blood flow by vascular surgery. Therefore, there is also a need to provide methods which accelerate the rate of the healing of chronic dermal skin ulcers before the onset of infection and without the need for expensive and invasive treatments such as surgery.

SUMMARY OF THE INVENTION

The present invention is based on the discovery that pseudopterosins or pseudopterosin derivatives accelerate the healing of a wide variety of wounds. It is now been found that when applied to a wound, pseudopterosins or pseudopterosin derivatives promote the growth and proliferation of keratinocytes, fibroblasts and endothelial cells. They also cause collagen matrix formation in the wound, which can result in reduced scarring. Based on this discovery, methods for promoting the healing of wounds are disclosed.

One embodiment of the present invention is a method of promoting the healing of a wound in an individual or animal. The method comprises contacting the wound with a composition comprising an effective wound healing amount of a compound having the structure in Formula I:

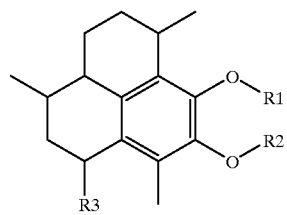

(I)

wherein:

R1 and R2 are selected from the group consisting of —H, lower alkyl, substituted lower alkyl, phenyl, substituted phenyl, benzyl, substituted benzyl, acyl, alkoxycarbonyl and a monosaccharide, and wherein R1 and R2 must be different, and one of R1 or R2 is a monosaccharide; and R3 is a substituted or unsubstituted lower alkyl group.

Another embodiment of the present invention is a method of promoting the growth and proliferation of keratinocytes, fibroblasts and endothelial cells in a wound on an individual or animal. The method comprises contacting the wound with a composition comprising an effective wound healing amount of a compound having the structure of Formula I.

The methods of the present invention are useful in accelerating the rate of wound healing on an individual or an animal. Shortened healing times can reduce the risk of infection, can reduce the losses of body fluids from burn wounds, and can result in fewer complications such as cellulitis, osteomyelitis and gangrene in diabetic patients. Accelerated wound healing can also bring about wound closure in patients with chronic skin ulcers. Better clinical outcomes can be obtained when the methods of the present invention are used to promote wound healing, e.g. reduced scarring, disfigurement and skin contraction.

DETAILED DESCRIPTION OF THE INVENTION

Figure 1:
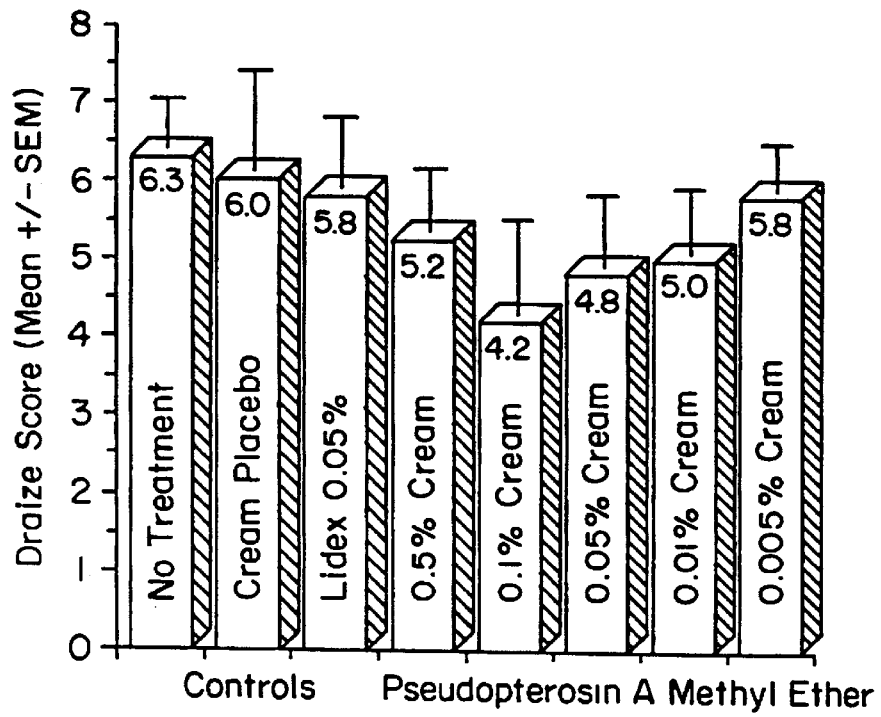
FIG. 1 is a graph illustrating the wound healing effect of pseudopterosin A methyl ether in a cream formulation compared with controls on skin lesions which had been chemically induced on the backs of guinea pigs.

The method of present invention can be used to promote the healing of a wide variety of wounds, including wounds to external epithelial tissue, internal epithelial tissue, dental tissue and eye tissue. Wounds to external epithelial tissue are preferred and are of several types: excisional, burns, dermal skin ulcers, lesions due to dermatological diseases, and atopic dermititus due to immediate type hypersensitivity.

Excisional wounds include tears, cuts, punctures or lacerations in the epithelial layer of the skin and may extend into the dermal layer and even into subcutaneous fat and beyond. Excisional wounds can result from surgical procedures or from accidental penetration of the skin.

Burn wounds refer to cases where large surface areas of skin have been removed or lost from an individual. The loss of skin refers to the epidermal layer, and usually includes the dermal layer. Wounds of this type include cases where part of the dermis has been lost or where the wound penetrates to subcutaneous fat and beyond. A burn wound can also result when an individual's skin is exposed to a chemical agent. Typically, burn wounds result when a large area of an individual's skin is exposed to heat, such as in a fire. As used herein, burn wounds also include cases where large areas of the skin have been removed through abrasion or surgically, e.g. to remove a skin cancer or to provide a skin autograft.

Dermal skin ulcers refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

"Dental tissue" refers to tissue in the mouth which is similar to epithelial tissue, for example gum tissue. Thus, the method of the present invention is useful for treating periodontal disease. "Internal epithelial tissue" refers to tissue inside the body which has characteristics similar to the epidermal layer in the skin. Examples include the lining of the intestine. Consequently, the method of the present invention is useful for promoting the healing of certain internal wounds, for example wounds resulting from surgery. A "wound to eye tissue" refers to severe dry eye syndrome, corneal ulcers and abrasions and ophthalmic surgical wounds.

Wounds caused by dermatological diseases include lesions resulting from autoimmune disorders such as psoriasis. Atopic dermititis refers to skin trauma resulting from allergies associated with an immune response caused by allergens such as pollens, foods, dander, insect venoms and plant toxins.

A method which "promotes the healing of a wound" results in the wound healing more quickly as a result of the treatment than a similar wound heals in the absence of the treatment. "Promotion of wound healing" can also mean that the method causes the proliferation and growth of keratinocytes, fibroblasts and endothelial cells, or that the wound heals with less scarring, less wound contraction, less collagen deposition and more superficial surface area. In certain instances, "promotion of wound healing" can also mean that certain methods of wound healing have improved success rates, (e.g. the take rates of skin grafts,) when used together with the method of the present invention. The method can promote the healing of wounds on humans and animals such as dogs, farm animals, guinea pigs, cats and the like.

The composition used in the present invention to promote wound healing comprises an effective wound healing amount of a pseudopterosin or a pseudopterosin derivative. The pseudopterosins are a class of natural products isolated from the sea whip Pseudopterogorgia (Look et al., *J. Org. Chem.* 51:5140 (1986). These compounds are structurally related to aglycon (1), having an aldose sugar bonded to one of the phenols of the tricyclic ring system of (1) through a glycoside linkage at is anomeric center. A numbering system for the ring carbons of the aglycon is indicated in (1).

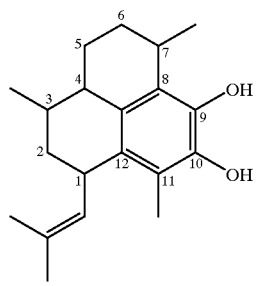

(1)

Examples of pseudopterosins include pseudopterosins A–D (2–5), which were the first compounds of this class to be isolated (Look et al., *J. Org. Chem.* 51:5140 (1986). Recently, a series of pseudopterosins having structural differences from pseudopterosins A–D were isolated from *P. elisabethae* (Roussiss et al., *J. Org. Chem.* 55:4916 (1990)). The sugar moiety in pseudopterosin E (6) and F (7) is attached to the phenol at carbon 10 of the aglycon instead of the phenol at carbon 9, as in pseudopterosins A–D. In pseudopterosins G–J (8–11), the stereochemical configuration at carbon 7 of the aglycon is inverted with respect to pseudopterosins A–D. The aglycon of pseudopterosins K (13) and L (14) is enantiomeric to the aglycon of pseudopterosins A–D. Pseudopterosin derivatives are also useful for the methods described herein. As used herein, a pseudopterosin derivative is a pseudopterosin in which the aglycon (1) and/or the monosaccharide substructures are chemically modified and which promotes wound healing. Examples of pseudopterosin derivatives include pseudopterosins in which-the free phenol of the aglycon is alkylated or acylated and are referred to herein as "pseudopterosin alkyl ethers" or "acylated pseudopterosins", respectively. Specific examples of pseudopterosin A derivatives include pseudopterosin A methyl ether (15) (R2=—$CH_3$), pseudopterosin A 4-hydroxybutyl ether (R2=(—$CH_2$)$_4$—OH)), pseudopterosin A pentyl ether (R2=—($CH_2$)$_4$—$CH_3$), pseudopterosin A acetamide ether (R2=—$CH_2$CO—$NH_2$), and pseudopterosin A benzyl ether (R2=—$CH_2$—$C_6H_5$). Pseudopterosin derivatives also include pseudopterosins wherein the hydrocarbon side chain attached to carbon one is modified, for example by hydrogenation, or by oxidation of the 2-methyl-1-propene moiety to, for example, 1-keto-2-methyl-propane or 2-methyl-propeneoxide (Jacobs, et al., U.S. Pat. No. 4,849,410). Chain elongation of these

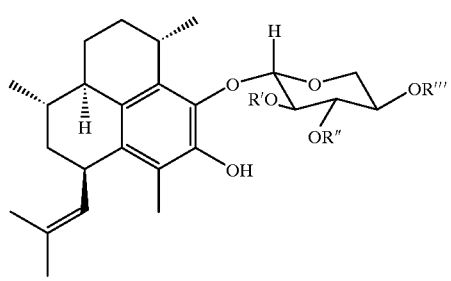

(2) R', R" and R'" = H (Pseudopterosin A)
(3) R' = Ac and R" and R'" = H (Pseudopterosin B)
(4) R" = Ac and R' and R'" = H (Pseudopterosin C)
(5) R'" = Ac and R" and R'" = H (Pseudopterosin D)

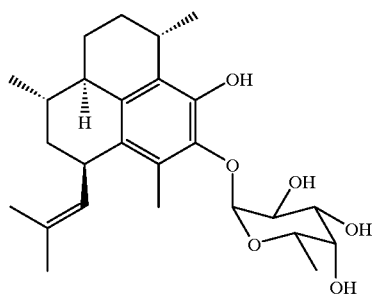

(6) (Pseudopterosin E)

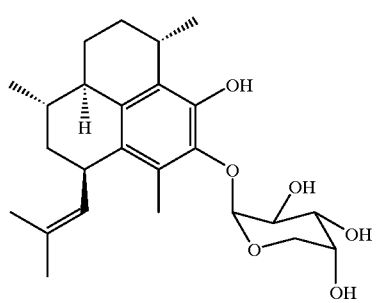

(7) (Pseudopterosin F)

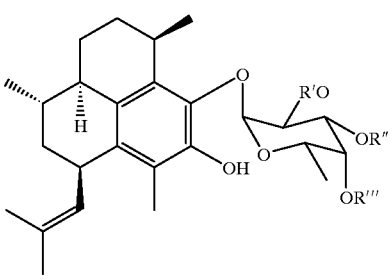

(8) R', R" and R'" = H (Pseudopterosin G)
(9) R' = Ac and R" R'" = H (Pseudopterosin H)
(10) R" = Ac and R' and R'" = H (Pseudopterosin I)
(11) R'" = Ac and R" and R'" = H (Pseudopterosin J)

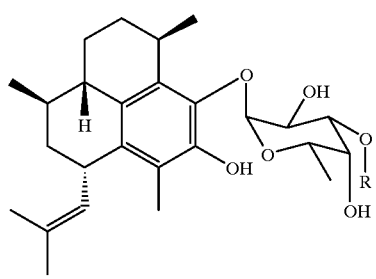

(13) R = H (Pseudopterosin K)
(14) R = Ac (Pseudopterosin L)

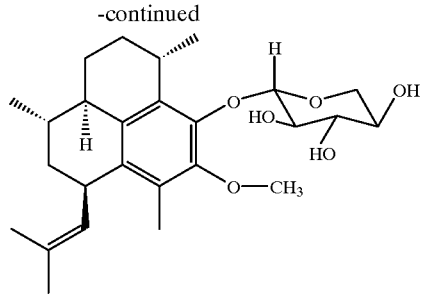

(15) Pseudopterosin A Methyl Ether oxidized pseudopterosins can be carried out by methods known to those skilled in the art.

In one embodiment the pseudopterosin or pseudopterosin derivative has the structure of Formula II:

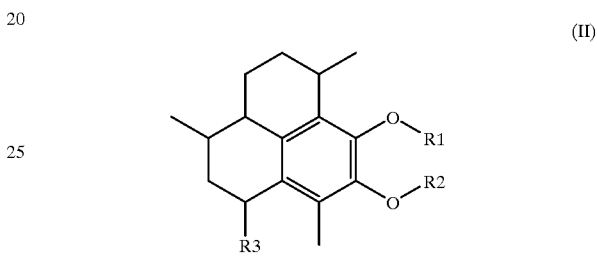

(II)

R1 and R2 are each selected from the group consisting of —H, lower alkyl, substituted lower alkyl, phenyl, substituted phenyl, benzyl, substituted benzyl, acyl, alkoxycarbonyl and a monosaccharide. R1 and R2 must be different and one of R1 and R2 is the monosaccharide.

R3 is a substituted or unsubstituted lower alkyl group. Preferably, R3 is —CH=C(CH$_3$)$_2$ or —CH$_2$CH(CH$_3$)$_2$.

As used herein, "lower alkyl" refers to a hydrocarbon containing one to about ten carbon atoms. The hydrocarbon can be saturated or can contain one or more units of unsaturation. The hydrocarbon can also be branched or straight chained.

Suitable substituents on a lower alkyl group include hydroxy, alkoxy, ketone, aldehyde, amide (—CO—NH$_2$), alkyl ester, alkyl amine, benzyl, substituted benzyl, phenyl, substituted phenyl, amine and the like. Suitable substituents on a phenyl or benzyl group include nitro, cyano, C1–C4 straight chain or branched alkyl, halo, alkoxy and the like.

An "acyl" group is —C(O)-(lower alkyl), wherein alkyl is as defined above. An "alkoxy carbonyl" group is —C(O)—O-(lower alkyl), wherein lower alkyl is as defined above.

The aglycon portion of the compound of the present invention has four chiral centers, resulting in sixteen possible stereoisomers. Preferred stereoisomers are those in which the stereochemical configurations at the four chiral carbons in the aglycon are the same as in pseudopterosin A (1), pseudopterosin G (8) or pseudopterosin K (13). The stereochemical configuration of pseudopterosin A is most preferred.

As used herein, a "monosaccharide" is a chiral polyhydroxy aldehyde in a cyclic hemiacetal form (referred to as an "aldose") or a chiral polyhydroxy ketone in a cyclic hemiketal form (referred to as a "ketose"). Chiral polyhydroxy aldehydes are preferred. Examples of suitable polyhydroxy aldehydes include aldotrioses, aldotetroses (e.g. D- and L-erythrose and threose), aldopentoses (e.g. D- and L-arabinose, xylose, ribose, and lyxose), aldohexoses (e.g. D- and L-glucose, allose, altrose, mannose, gulose, idose, galactose and talose), aldoheptoses, aldo-octoses and aldononoses. The polyhydroxy aldehyde can be in a furanose form (for aldoses having four carbons or more) or pyranose form (for aldoses having five carbon atoms or more). The pyranose form is preferred.

Suitable polyhydroxy ketones include pentuloses, hexuloses (e.g. D-fructose, D-sorbose, D-psicose and D-tagatose), heptuloses, octuloses and nonuloses. The polyhydroxy ketone can be in a furanose form (for ketoses having five carbons or more) or pyranose form (for ketoses having six or more carbon atoms). The pyranose form is preferred.

A "monosaccharide" can also include the monosaccharides described hereinabove in which one or more of the hydroxy groups are functionalized with an alcohol protecting group. More than one kind of alcohol protecting group can be used in a single monosaccharide. Suitable alcohol protecting groups include lower alkyl (preferably methyl), acyl (preferably acetyl), benzoyl, substituted benzoyl (suitable substituents include, for example, lower alkyl, nitro, halide, alkoxy and cyano) and carbonates. Other suitable protecting can be found in Greene and Wuts, "Protective Groups in Organic Synthesis," second edition, John Wiley and Sons, Inc., 1991. One or more hydroxy groups on these monosaccharides can be protected with alcohol protecting groups, as described above. The preferred alcohol protecting group is acetyl.

In a preferred embodiment the monosaccharide has the structure of Structural Formula III:

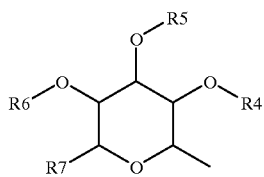

(III)

R4, R5 and R6 are independently selected from the group consisting of —H and an alcohol protecting group. Suitable alcohol protecting groups are described above. A preferred alcohol protecting group is acyl, and is even more preferably acetyl.

R7 is selected from the group consisting of —H, —CH$_3$ and —CH$_2$OR8. R8 is selected from the group consisting of —H, a lower alkyl group and an alcohol protecting group. Suitable lower alkyl and alcohol protecting groups are as described above. Acyl is a preferred alcohol protecting group, and acetyl is even more preferred.

In one aspect R1 is the monosaccharide, R3 is —CH═C(CH$_3$)$_2$ or —CH$_2$—CH(CH$_3$)$_2$, R4, R5 and R6 are each independently —H or acyl (preferably acetyl), and R7 is selected from the group consisting of —H, —CH$_3$ and —CH$_2$OH. Examples include compounds wherein the aglycon has the structure of pseudopterosin A (1), pseudopterosin G (8) and pseudopterosin K (13) and R1 is α-L-fucose, α-D-arabinose or β-D-xylose. One or more of the hydroxy groups on the monosaccharide moiety can be protected with an acyl group, preferably acetyl. Alternatively, R2 is the monosaccharide. Examples include compounds wherein the aglycon has the structure of pseudopterosin E (6) and the R2 is α-L-fucose, α-D-arabinase or β-D-xylose.

In a more preferred embodiment of the present invention, the compound which promotes wound healing has the structure of Structural Formula IV:

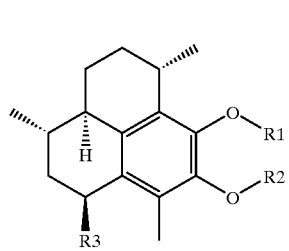

(IV)

R1 has the structure of Structural Formula V:

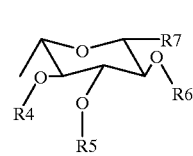

(V)

R2 is selected from the group consisting of —H, lower alkyl, benzyl, —(CH$_2$)$_m$-benzyl, —(CH$_2$)$_m$-(substituted benzyl), —(CH$_2$)$_m$—CH$_2$OH and —(CH$_2$)$_m$—CONH$_2$, wherein m is an integer from 1 to about 9; m is preferably an integer from 1 to 4. Preferred lower alkyl groups are C1–C6 straight chain, saturated hydrocarbons. It is most preferred that R2 is methyl or —H. R3 is —CH═C(CH$_3$)$_2$. R4, R5 and R6 are each independently selected from the group consisting of —H and acetyl. R7 is independently selected from the group consisting of —H —CH$_3$ and —CH$_2$OH. It is most preferred that R4, R6 and R7 are each —H, i.e. the compound is pseudopterosin A, pseudopterosin A methyl ether, pseudoptersoin C or pseudopterosin C methyl ether.

In another more preferred embodiment the compound which promotes wound healing has the structure of Structural Formula IV. R1 is selected from the group consisting of —H, lower alkyl, benzyl, —(CH$_2$)$_m$-benzyl, —(CH$_2$)$_m$-substituted benzyl, —(CH$_2$)$_m$—CH$_2$OH and —(CH$_2$)$_m$—CONH$_2$, wherein m is an integer from 1 to about 9. m is preferably 1–4. Preferred lower alkyl groups are C1–C6 straight chain saturated hydrocarbons. It is most preferred that R1 is methyl or —H. R2 has the structure of Structural Formula VI:

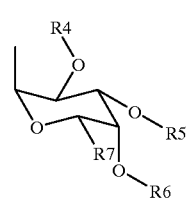

(VI)

R3 is —CH═C(CH$_3$)$_2$. R4, R5 and R6 are each independently selected from the group consisting of —H and acetyl. —H is most preferred. R7 is independently selected from the group consisting of —H —CH$_3$ and —CH$_2$OH. —CH$_3$ is most preferred.

Other examples of suitable compounds include pseudopterosin A benzyl ether, pseudopterosin A o-nitrobenzyl ether, pseudopterosin A pentyl ether, pseudopterosin A decyl ether, pseudopterosin A octadecyl ether, pseudopterosin A 4-hydroxy butylether, pseudopterosin A acetamide (wherein R2 in Formula IV is —CH$_2$—NH$_2$), pseudopterosin A tetraacetate, pseudopterosin B, pseudopterosin D, pseudopterosin B methyl ether, pseudopterosin D methyl ether, pseudopterosin A ethyl ether, pseudopterosin B ethyl ether, pseudopterosin C ethyl ether, pseudopterosin D ethyl ether, acetyl pseudopterosin A, acetyl pseudopterosin B, acetyl pseudopterosin C, acetyl pseudopterosin D, pseudopterosin E ethyl ether, acetyl pseudopterosin E, pseudopterosin F, pseudopterosin F methyl ether, pseudopterosin F ethyl ether, acetyl pseudopterosin F, pseudopterosin G, pseudopterosin G methyl ether, pseudopterosin G ethyl ether, acetyl pseudopterosin G, pseudopterosin H, pseudopterosin H methyl ether, pseudopterosin H ethyl ether, acetyl pseudopterosin H, pseudopterosin I, pseudopterosin I methyl ether, pseudopterosin I ethyl ether, acetyl pseudopterosin I, pseudopterosin J, pseudopterosin J methyl ether, pseudopterosin J ethyl ether, acetyl pseudopterosin J, pseudopterosin K, pseudopterosin K methyl ether, pseudopterosin K ethyl ether, acetyl pseudopterosin K, pseudopterosin L, pseudopterosin L methyl ether, pseudopterosin L ethyl ether and acetyl pseudopterosin L.

Pseudopterosin A, C and E are isolated from *Pseudopterogorgia elisabethae* according to known procedures (Look et al., *J. Org. Chem.*, 51:5140 (1986) and Roussis et al., *J. Org. Chem.*, 55:4916 (1990)). Alkyl ethers of pseudopterosins are prepared by alkylating the pseudopterosin with an alkylating agent such as methyl iodide (Look et al., Roussis et al. and Jacobs et al. U.S. Pat. No. 4,849,410). Pseudopterosin B–L and alkylated derivatives thereof can be isolated and prepared by the same basic procedures (Look et al. and Jacobs et al. U.S. Pat. No. 4,745,104, Jacobs et al. U.S. Pat. No. 4,849,410 and Roussis et al.). Methods of preparing pseudopterosin derivatives having other monosaccharides are carried out by methods known in the art (Corey and Carpino, *J. Am. Chem. Soc.*, 111:5472 (1989)). Examples of the preparation of other pseudopterosin derivatives are given in Examples 4–9 and discussed further in U.S. patent application filed Jun. 7, 1995, now U.S. Pat. No. 5,624,911 naming William H. Fenical and Robert S. Jacobs as inventors, the teachings of which are incorporated herein by reference.

The composition used in the present invention to promote wound healing can additionally comprise an inert, non-toxic solvent such as acetone or alcohol in which the pseudopterosin or pseudopterosin derivative is dissolved, or, preferably, a pharmaceutical carrier suitable for local topical administration in which the pseudopterosin or pseudopterosin derivative is dissolved or suspended. Examples of pharmaceutically acceptable carriers include, for example, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

Preferred formulations are those which promote penetration of dermal and epidermal layers of the skin by the pseudopterosin or pseudopterosin derivative and in which the pseudopterosin or pseudopterosin derivative is stable. A preferred formulation is a petrolatum ointment comprising from between about 0.005% to about 2.0% of the pseudopterosin or pseudopterosin derivative, e.g. pseudopterosin A methyl ether. The ointment is prepared according to the procedure in Example 3 and has the following composition:

|  | % W/W |
| --- | --- |
| White Petrolatum, USP | 82.5–84.5 |
| White Wax, NF | 10.0 |
| Cholesterol, NF | 3.0 |
| Diisopropyl Adipate | 2.5 |
| Pseudopterosin | 0.005–2.0 |

Another preferred formulation is an oil/water cream with between about 0.005% and about 2.0% pseudopterosin or pseudopterosin derivative having the following composition:

| Stearic Acid | 8.0% |
| --- | --- |
| Cetyl Alcohol | 0.8% |
| Polyoxyethylene Laurel Ether (BRIDGE 30 ™) | 1.5% |
| Octyldodecanol | 14.4% |
| Carboxyvinyl Polymer (CARBOMER 980 ™) | 0.6% |
| Sodium Laureth Sulfate | 0.3% |
| Sodium Hydroxide | 1.2% |
| Methylparaben | 0.2% |
| Propylparaben | 0.05% |
| Pseudopterosin | 0.005–2.0% |
| Purified Water | 70.95–72.95% |

Both of these preferred formulations with 0.5% pseudopterosin A methyl ether provide stability greater than six months at room temperature.

The wound being treated is contacted with a composition comprising an effective wound healing amount of a pseudopterosin or pseudopterosin derivative, for example by applying the composition directly to the wound. In the case of wounds to eye tissue, the compound can optionally be applied by eye drops.

An "effective wound healing amount of a pseudopterosin or a pseudopterosin derivative" contains a sufficient quantity of the pseudopterosin or a pseudopterosin derivative to promote wound healing and the growth and proliferation of endothelial cells, keratinocytes and fibroblasts. The skilled artisan will appreciate that the quantity of pseudopterosin or a pseudopterosin derivative which promotes wound healing depends on the specific nature of the wound, e.g. wound type and severity, and can vary the amount of compound used, depending on the application. The amount of pseudopterosin or pseudopterosin derivative applied to the wound depends on the amount of the composition (e.g., inert solvent and pharmaceutical carrier) applied to the wound and the concentration of the pseudopterosin or pseudopterosin derivative in the pharmaceutical carrier or inert solvent. Generally, enough pharmaceutical carrier or inert solvent is used to cover the wound. Suitable concentrations of pseudopterosin or pseudopterosin derivative in the pharmaceutical carrier or inert solvent ranges from about 0.005% to about 2.0%, preferably from about 0.05% to about 0.5%.

In certain instances where wounds are being treated, it may be advantageous to co-administer one or more additional pharmacologically active agents to the wound along with the compounds of the present of invention. For example, infection is a threat with any open wound, particularly in burn wounds. One aspect of the present invention is to co-administer to the wound an antimicrobial, a disinfectant or an antibiotic. Managing pain and inflammation are also important aspects of treating wounds. The compounds of the present invention can also be co-administered to the wound along with a pain-relieving agent such as an analgesic or an anti-inflammatory agent.

Another embodiment of the present invention is a method of improving the take rate of a skin graft. Because there is no dermis or basement membrane present at the time an epithelial autograft is applied to a wound, there is nothing to secure the autograft to the wound bed. Consequently, autografts tend to blister and shear, decreasing the likelihood that the autograft will "take", i.e. adhere to the wound and form a basement membrane with the underlying granulation tissue. Take rates can be increased by providing a physiological scaffolding in the wound onto which keratinocytes and endothelium cells can migrate and by promoting the formation and migration of capillaries into the scaffolding. Pseudopterosin A methyl ether has been observed (Example 1) to promote the growth and proliferation of fibroblasts and the neovascularization of wounds. Increased collagen biosynthesis and deposition results, thereby forming a collagen matrix scaffolding within the wound. Consequently, the application of a pseudopterosin or pseudopterosin derivative to a wound also promotes the processes necessary to increase the take rates of skin autografts. The method of increasing take rates comprises contacting the skin autograft with an effective wound healing amount of the compounds and compositions described in the method of promoting wound healing and in the method of promoting the growth and proliferation of keratinocytes, fibroblasts and endothelial cells in a wound, as described above.

The invention is further illustrated by the following examples, which are not intended to be limiting in any way.

EXEMPLIFICATION

EXAMPLE 1

Healing of Full Thickness Lesions on Hartley Guinea Pigs Promoted by Pseudorterosin A Methyl Ether Full thickness lesions were induced on the backs of Hartley Strain guinea pigs (Skoog, M. L. *Acta Derm Venerol* (Stockh) 60(3):239–44, 1980) by the cutaneous application of 1-chloro-2,4-dinitrobenzene (DNCB). Shaved Hartley male guinea pigs were treated once daily for four days with 1–2% DNCB in acetone to induce the full thickness wounds involving both dermal and epidermal portions. The DNCB caused the loss of the epidermis thus subjecting the dermis to conditions not suitable for the maintenance of continued viability. Dermal appendages were necrotic, degenerating or lost. The remnants of the dermis were found to be acellular and edematous. These severe defects encompassed a significant area of the demarcated region of irritant application and lacked integrity of the epithelial barrier. The lesions and treatment area were approximately 9 $cm^2$. Animals in each group were treated with a cream formulation (See Example 2) containing 0.005%, 0.01%, 0.05%, 0.1% or 0.5% pseudopterosin A methyl ether. Control,groups in which the animals were treated with 0.05% fluocinonide (commonly sold under the trade name LIDEX™), a cream placebo or were left untreated were also included.

In a second set of experiments, animals were treated with an ointment (See Example 3) containing 0.1% or 0.05% methyl pseudoterosin A. Animals treated with an ointment placebo or left untreated were used as controls.

On days 5–9 animals were scored on a blind basis by two independent observers using the Draize Criteria (Draize, J. H., Dermal Toxicity, "Appraisal of the Safety of Chemicals in Food, Drugs, and Cosmetics," The Association of Food and Drug Officials of the United States, 46–59, 1959). The Draize Criteria reflects erythema, edema, and other clinical parameters. Control and treatment groups contained six animals. The mean value reflects the Draize score obtained on day 9. The results are shown in FIG. 1. Results were compared by unpaired, nonparametric analysis.

Figure 2:
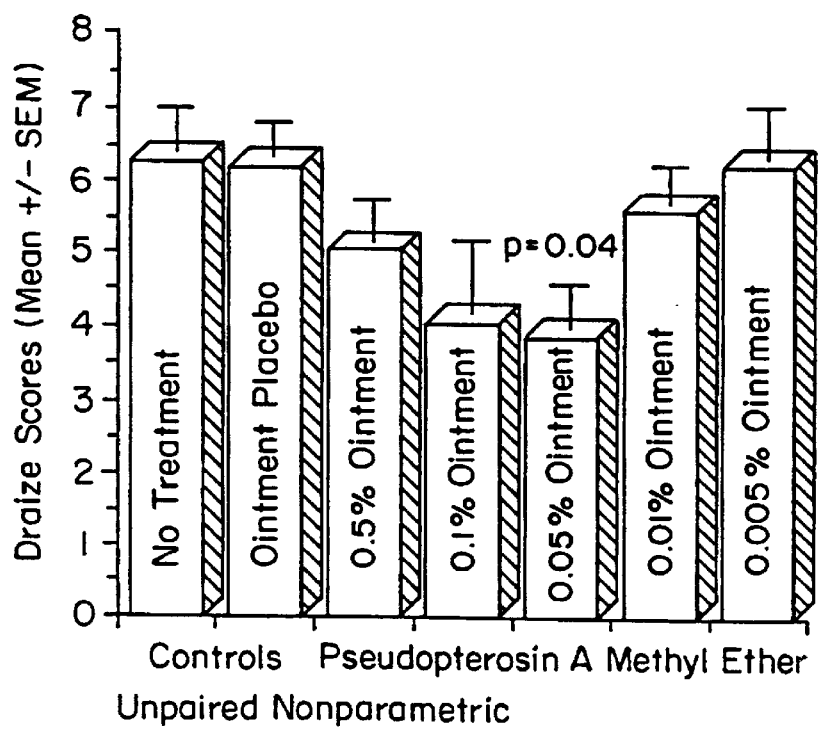
FIG. 2 is a graph illustrating the wound healing effect of pseudopterosin A methyl ether in an ointment compared with controls on skin lesions which had been chemically induced on the backs of guinea pigs.

The effects of pseudopterosin A methyl ether (cream formulation) in reducing erythema and edema and in promoting regrowth of tissue were noticeably superior to the effect of the steroid placebo controls. FIG. 1 and FIG. 2 show that pseudopterosin A methyl ether in the cream formulation and in the ointment demonstrated a dose response relationship with respect to its ability to decrease the DNCB-induced inflammation. Placebo ointment and cream vehicles were found to lack clinical efficacy.

Skin harvested from the central portion of the lesions from non-treated animals or placebo controls revealed delamination and loss of the epidermis, necrosis of hair follicles, sweat glands and other dermal appendages, fibroblast necrosis, edema of the dermis and other manifestations of severe full thickness skin lesions. The skin appeared non-viable since viable cellular elements were not observed. Clinically and histopathologically, the necrotic lesion induced by the chemical irritant, coupled with the host response, resulted in tissue destruction and loss of the epidermis.

Microscopic examination of skin taken from animals treated with clobetasol propionate (Temovate™) was similar to untreated or placebo treated animals. Loss of the epidermis was confirmed histologically in nearly all cases. The apical regions of the dermis were judged to be non-viable with remnants of inflammatory foci and necrotic fibroblasts. Dermal appendages including hair follicles, sebaceous and sweat glands, and other dermal components were noted to be necrotic or lost. Deeper zones of the dermis appeared to contain viable fibroblasts with minimal, patent vasculature. Considerable edema was noted in the dermis.

In contrast to the untreated or placebo treated animals, all animal treated with pseudopterosin A methyl ether displayed the presence of a hypertrophic epidermis. Histopathological assessment of the hypertrophic epidermis was confirmed by the increase in the thickness of the epidermis, increased thickness of the stratum granulosum and the presence of nuclear remnants within the stratum corneum. In addition, frequent mitotic figures were noted within the basal keratinocytes. The dermis from animals treated with pseudopterosin A methyl ether displayed active patterns of fibroblast proliferation, neovascularization, and new collagen matrix deposition. This aggressive repopulation of the dermis took place within the context of existing dermal structure thus limiting or preventing apparent scar formation. The striking picture of neovascularization, as evidenced by dilated capillary vasculature with prominent endothelium, indicates that an active process was mediated by pseudopterosin A methyl ether in these animals. Clinical observation confirmed that epidermal regrowth including hair was accomplished by proliferation of dermal appendageal epithelial derivatives. In contrast to untreated animals having focal necrosis with active bleeding and considerable eschar, animals treated with pseudopterosin A methyl ether displayed nearly complete resolution of lesions.

Animals treated with pseudopterosin A methyl ether displayed significant and consistent evidence of wound healing. The final outcome clearly reveals a continuous epithelial barrier and dermal component of skin that is consistent with active cellular proliferative responses typical of wound healing. Keratinocytes, dermal fibroblasts and capillary endothelium are all recognized in patterns consistent with an active resolution phase secondary to injury and tissue destruction. These cellular elements are proliferative and nuclear morphology indicated considerable biosynthetic activity. Epidermis was noted to be hypertrophic, another common feature of wound healing.

Increased matrix formation through collagen deposition typically results in reduced scarring (Ehrlich, *J. of Trauma*, 24(5):35 (1984) and Ehrlich, *Prog. Clin. Biol. Res.*, 266:243 (1988)), suggesting that treatment of wounds with a pseudopterosin or a pseudopterosin derivative gives a better clinical outcome as well as accelerated healing rates. This was confirmed by visual observation of healed wounds which had been treated with pseudopterosin A methyl ether. As expected, these wounds were characterized by larger surface areas and decreased scarring.

EXAMPLE 2

Preparation of a Pseudopterosin Ointment Formulation

|  | % W/W |
|---|---|
| White Petrolatum, USP | 84.0 |
| White Wax, NF | 10.0 |
| Cholesterol, NF | 3.0 |
| Diisopropyl Adipate | 2.5 |
| Pseudopterosin | 0.5 |

Pseudopterosin A methyl ether was added to diisopropyladipate and mixed well until dissolved. The mixture was sonicated to increase the speed of dissolution. All other components were combined in a suitable vessel and heated to approximately 75° C. After all components are melted, the combination was mixed with a propeller mixer while allowing to cool. While continuing to propeller mix, the pseudopterosin A methyl ether substance solution was incorporated into the ointment base when the ointment had cooled to about 50° C. The mixture was cooled to room temperature, using intermittent hand stirring to ensure product uniformity.

EXAMPLE 3

Preparation of a 0.1% Ointment of Pseudopterosin A Methyl Ether

White petrolatum (82.4 grams), white wax (10.0 grams) and cholesterol (3.0 grams) were weighed, added to a stainless steel vessel and mixed with a homogenizing mixer for five minutes at high speed. Mixing was continued at low speed while cooling to 50° C. by exposure to ambient air.

Diisopropyl adipate (2.5 grams) was weighed into a separate container. Pseudopterosin A methyl ether (0.1 grams) was added and mixed at 45° C. to 50° C. with stirring until completely dissolved. The warm diisopropyl adipate solution was added to the ointment base at about 50° C. The resulting batch was further mixed for five minutes with the homogenizing mixer at high speed. The batch was then allowed to cool below 30° C. in a room temperature water bath while mixing to maintain product consistency.

EXAMPLE 4

Synthesis of Pseudopterosin A Benzyl Ether

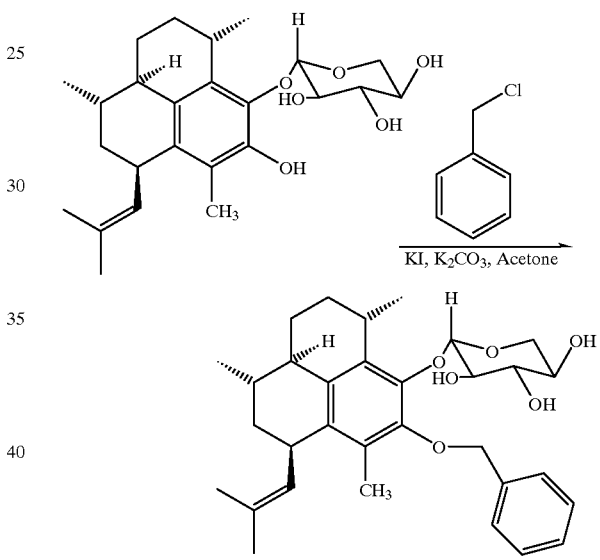

Preparation

Pseudopterosin A (150 mg in 50 ml acetone) was placed in a 100 ml flask. $K_2CO_3$ (150 mg), sodium iodide (500 mg) and benzylchlorine (1.1 g=1 ml) were added. The solution was stirred and refluxed for 5 hours. After stirring overnight, 0.5 ml benzylchlorine was added and the solution was refluxed for another 6 hours. After cooling to room temperature, the yellow solution was concentrated by rotary evaporation. Water (50 ml) and $CH_2Cl_2$ (30 ml) were added to the concentrate and the solution was transferred to a separatory funnel and extracted 3 times with $CH_2Cl_2$ (3×50 ml). The total collected $CH_2Cl_2$ layer were washed with brine (3×50 ml). Next, the solution was transferred to an Erlenmeyer flask and dried with $Na_2SO_4$. The dry solution was filtered and concentrated under vacuum to give a yellow oil.

Purification

For purification, the yellow oil was chromatographed on a silica column eluting with 65/35 ethyl acetate/isooctane. The product was dried under high vacuum to give white crystals. Yield: 90 mg=50%.

EXAMPLE 5

Synthesis of Pseudopterosin A Pentyl Ether

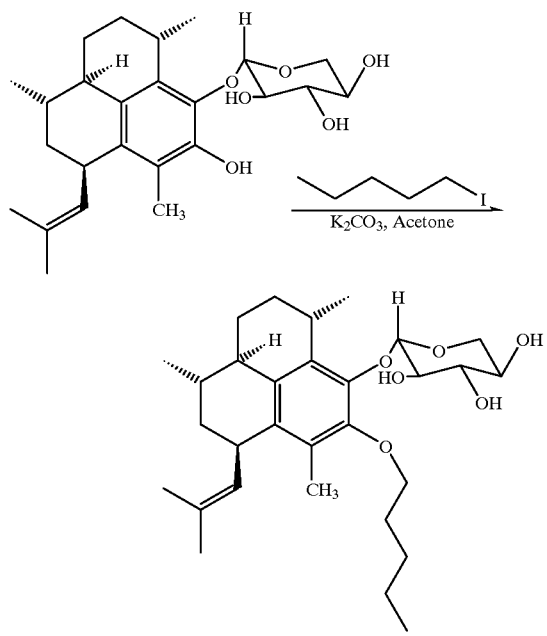

Preparation

Pseudopterosin A (150 mg in 70 ml acetone) was placed in a 100 ml flask. $K_2CO_3$ (150 mg) and 1-iodopentane (1400 mg=0.92 ml) were added. The solution was stirred and refluxed overnight. After cooling to room temperature, the solution was concentrated by rotary evaporation. Water (30 ml) and $CH_2Cl_2$ (30 ml) were added to the concentrate and the solution was transferred to a separatory funnel and extracted 3 times with $CH_2Cl_2$ (3×30 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give a yellow oil.

Purification

For purification, the yellow oil was chromatographed on a silica column eluting with 50/50 ethyl acetate/isooctane. The product was dried under high vacuum to give white crystals. Yield: 84 mg=49%.

EXAMPLE 6

Synthesis of Pseudopterosin A Decanyl Ether

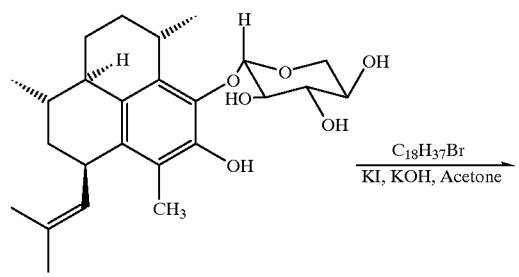

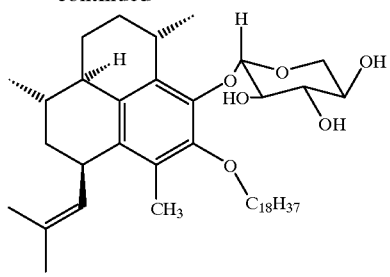

Pseudopterosin A (150 mg in 100 ml acetone) was placed in a 250 ml flask. $K_2CO_3$ (150 mg) and 1-iododecane (930 mg −0.74 ml) were added. The solution was stirred and refluxed for 5 hours. After stirring overnight, 0.74 ml 1-iododecane and 150 mg $K_2CO_3$ were added again and the solution was refluxed for another 15 hours. After cooling to room temperature, the solution was concentrated by rotary evaporation. Water (50 ml) and $CH_2Cl_2$ (50 ml) were added to the concentrate and the solution was transferred in a separatory funnel and extracted 3 times with $CH_2Cl_2$ (3×75 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give a yellow oil.

Purification

For purification, the yellow oil was chromatographed on a silica column eluting with 50/50 ethyl acetate/isooctane. The product was dried under high vacuum to give white crystals. Yield: 105 mg=52%.

EXAMPLE 7

Synthesis of Pseudopterosin A Octadecanyl Ether

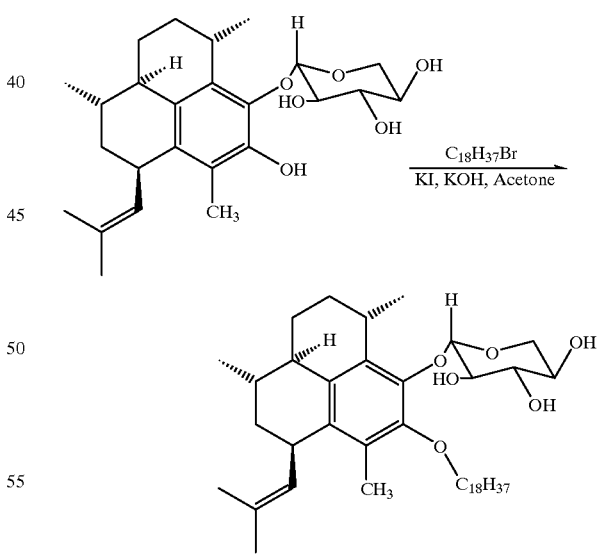

Pseudopterosin A (150 mg in 70 ml acetone) was placed in a 100 ml flask. $K_2CO_3$ (1150 mg), sodium iodide (580 mg) and 1-bromooctadecane (2300 mg) were added. The solution was stirred and refluxed overnight. After adding 25 ml toluene, the solution was again placed in a 100 ml flask. $K_2CO_3$ (1150 mg), sodium iodide (580 mg) and 1-bromooctadecane (2300 mg) were added. The solution was stirred and refluxed overnight. After adding 25 ml toluene, the solution was again stirred and refluxed overnight. Next, 25 ml water and 1000 mg of $K_2CO_3$ were added, and the solution was stirred and refluxed for another 5 hours. After cooling to room temperature, the solution was concentrated by rotary evaporation. Water (50 ml) and $CH_2Cl_2$ (30 ml) were added to the concentrate and the solution was transferred in a separatory funnel and extracted 3 times with $CH_2Cl_2$ (3×50 ml). The total collected $CH_2Cl_2$ layers were washed with brine (3×50 ml). Next, the solution was transferred into an Erlenmeyer flask and dried with $Na_2SO_4$. The dry solution was filtered and concentrated by rotary evaporation to give a yellow oil.

Purification

For purification, the yellow oil was chromatographed on a silica column eluting with 40/60 ethyl acetate/isooctane. The product was dried under high vacuum to give white crystals Yield: 100 mg=42%.

EXAMPLE 8
Synthesis of Pseudopterosin A Butanol Ether

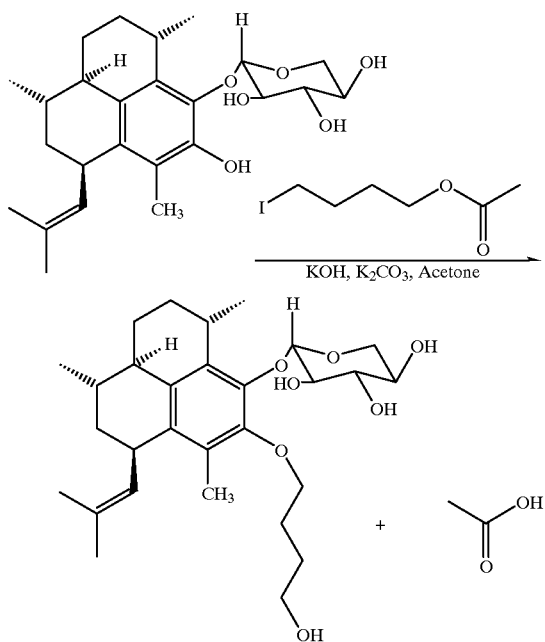

Preparation

Pseudopterosin A (150 mg in 50 ml acetone) was placed in a 100 ml flask. $K_2CO_3$ (150 mg) and 4-iodobutyl acetate (1300 mg=0.8 ml) were added. The solution was stirred and refluxed overnight. Then, iodobutyl acetate (650 mg=0.4 ml) and water (2.5 ml) were added and the solution was stirred and refluxed for another 5 hours. Then, 600 mg of KOH were added, and the solution was concentrated by rotary evaporation. Water (50 ml) and $CH_2Cl_2$ (30 ml) were added to the concentrate and the solution was transferred in a separatory funnel and extracted 3 times with $CH_2Cl_2$ (3×50 ml). The total collected $CH_2Cl_2$ layers were washed with brine (3×50 ml). Next, the solution was transferred to an Erlenmeyer flask and dried with $Na_2SO_4$. The dry solution was filtered and concentrated under vacuum to give yellow oil.

Purification

For purification, the yellow oil was chromatographed on a silica column eluting with 65/35 ethyl acetate/isooctane. The product was dried under high vacuum to give white crystals. The product was not the expected PsA acetoxy butyl ether but the PsA butanol ether, derived by saponification of the acetate under the basic conditions employed in the reaction. Yield: 46 mg=26%.

EXAMPLE 9
Synthesis of Pseudopterosin A Acetamide Ether

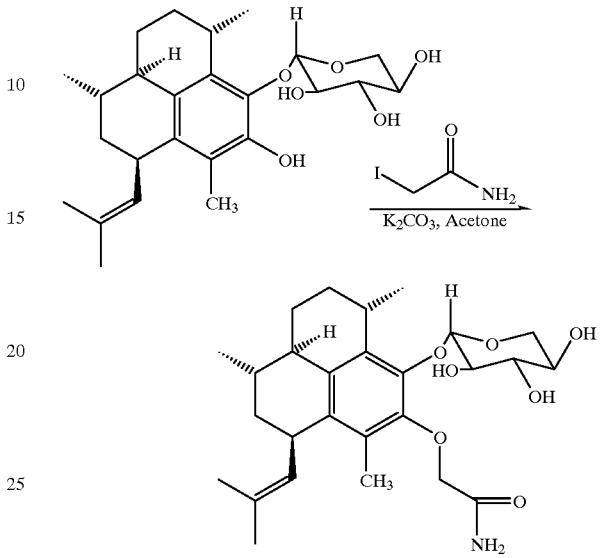

Preparation

Pseudopterosin A (150 mg in 50 ml acetone) was placed in a 100 ml flask. $K_2CO_3$ (1500 mg) and iodoacetamide (960 mg) were added. The solution was stirred and refluxed for 5 hours. After cooling to room temperature, the yellow solution was concentrated by rotary evaporation. Water (50 ml) and $CH_2Cl_2$ (30 ml) were then added to the concentrate and the solution was transferred in a separatory funnel and extracted 3 times with $CH_2Cl_2$ (3×50 ml). The total collected $CH_2Cl_2$ layers were washed with brine (3×50 ml). Next, the solution was transferred into a Erlenmeyer flask and dried with $Na_2SO_4$. The dry solution was filtered and concentrated under vacuum to give a yellow oil.

Purification

For purification, the yellow oil was chromatographed on a silica column eluting with 97/3 ethyl acetate/isooctane. The product was dried under high vacuum to give white crystals. Yield: 67 mg=40%.

EXAMPLE 10
Effects of Pseudopterosin A Methyl Ether Ointment on Normal Porcine Model One 20 kg domestic Yorkshire Pig was used for the study described below. The animal received general inhalation anesthesia and was placed in a prone position. The dorsum was shaved and cleansed.

A series of 64×1 $cm^2$ grids was tattooed onto the dorsum of the animal. The dorsum was covered with an occlusive dressing and the animal was awakened without difficulty.

After a 48 hour recovery period (to allow resolution of any skin irritation from creation of the grids), the pseudopterosin A methyl ether ointment was applied topically in concentrations of 0.05%, 0.15% and 0.5%. Vehicle alone and untreated skin served as controls. Ointment was applied to a 1 $cm^2$ square such that the surface area was completely covered. Ointment was applied at daily intervals for five days.

Elliptical biopsies were taken at day 1, 3, 5 and 7 days post application of the ointment. Biopsies were bisected along the long axis. Tissue was placed in formaldehyde for histology (H&E) and frozen in OCT freezing compound for further immunohistochemical analysis (ki-67 staining for proliferation). An occlusive dressing was reapplied each day after application of the ointment.

Gross observations of all treated and control sites revealed normal-appearing skin at all time points. No scaling, or erythema was noted. Histologic analysis revealed normal skin structure at all time points for all site biopsied. There were no signs of inflammatory infiltration or changes in epidermal architecture. Staining for Ki-67 also revealed similar proliferative patterns across all treatment groups.

Topical application of pseudopterosin A methyl ether (at concentrations of 0.05–0.5%) had no observable effect on normal porcine skin. No irritation was observed, nor was any inflammation induced by application of pseudopterosin A methyl ether.

EXAMPLE 11
Ability of Pseudopterosin A Methyl Ether Ointment to Promote Re-Epithelization of Partial Thickness Wounds One 20 kg Yorkshire pig was used for the study described below. The animal received general inhalation anesthesia and was placed in a prone position. The dorsum was shaved and cleansed. A series of partial thickness wounds (approximately 4 cm$^2$) was created on the dorsum using a dermatome set at 0.015 inches in depth. The wounds were placed on the back in mirror image array so that each treatment site had it own vehicle control site. The reason for mirror image wound placement was to control for the variability of healing that occurs depending upon the anatomic location of the wound.

Immediately after wounding, pseudopterosin A methyl ether ointment was applied as a single application to the wounds in concentrations of 0.05%, 0.15% and 0.5%. Vehicle alone, and untreated wounds were also studied. Ointment was applied such that it evenly covered the wound area. Following treatment, all wounds were covered with a semi-permeable occlusive dressing (OpSite) followed by a bolster dressing. Photographs and elliptical biopsies (including normal tissue margins) were taken on days three and eight post-wounding. An occlusive dressing was reapplied after day 3. Biopsies were bisected. One part was fixed in formalin, embedded in paraffin for routine histologic staining by hematoxylin and eosin (H&E). The second part was snap frozen and cryosat sections made for immunohistochemical reaction with the proliferative marker Ki-67.

The percent of re-epithelialization of each wound was quantitated by using a reticle grid in the eyepiece of a Labophot Nikon microscope. The proliferative activity was quantitated by immunohistochemical staining of frozen tissue sections with Ki-67 following by scoring of Ki-67 immunoreactive cells.

As expected, wounds treated with the vehicle alone, showed very little re-epithelialization (1.4±11.6%) on day three post-wounding (The Table). Within three days after a single application of pseudopterosin A methyl ether to individual wounds however, differences in the percent re-epithelialization across the wound were of served. There was a dose dependent, increase in the percent re-epithelialization of wounds treated with increasing concentrations of pseudopterosin A methyl ether suggesting an acceleration in the rate of healing of such wounds (The Table).

By day eight all wounds (including vehicle-treated wounds) were healed and showed similar histologic appearance.

TABLE

Percent Re-epithelialization of Partial Thickness Wounds Three Days After Treatment with a Single Application of Pseudopterosin A Methyl Ether

| Dose of Pseudopterosin A Methyl Ether (%) | Percent Re-epithelialization (Mean % + SEM) |
|---|---|
| 0 (vehicle control) | 14 ± 11.6 |
| 0.05 | 14 ± 7.3 |
| 0.15 | 27 ± 8.0 |
| 0.5 | 48 ± 9,7 |

The data presented here suggest that a single treatment with pseudopterosin A methyl ether may accelerate the rate of partial thickness wound healing.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of promoting the re-epithelization of a partial thickness wound on an individual or animal comprising contacting the wound with a composition comprising an effective wound healing amount of a compound having the following structural formula:

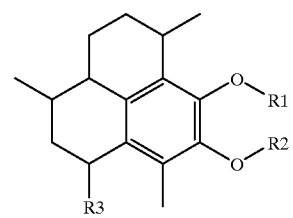

wherein:

R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

2. The method of claim 1 wherein the compound has the following structural formula:

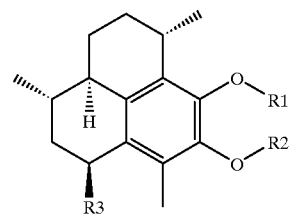

wherein

R1 has the following structural formula:

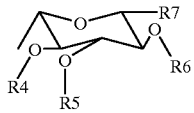

R2 is selected from the group consisting of —H, lower alkyl, benzyl, —(CH$_2$)$_m$—CH$_2$OH, —(CH$_2$)$_m$—CO—NH$_2$, —(CH$_2$)$_m$-(benzyl) and —(CH$_2$)$_m$-(substituted benzyl), wherein m is an integer from 1 to about 9;

R3 is —CH=C(CH$_3$)$_2$;

R4, R5 and R6 are independently selected from the group consisting of —H and acetyl; and R7 is selected from the group consisting of —H, —CH$_3$ and —CH$_2$OH.

3. The method of claim 1 wherein the compound has the following structural formula:

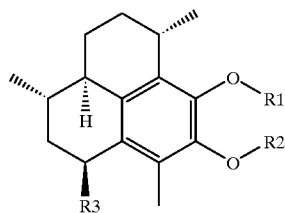

wherein

R1 is selected from the group consisting of —H, lower alkyl, benzyl, —(CH$_2$)$_m$—CH$_2$OH, —(CH$_2$)$_m$—CO—NH$_2$, —(CH$_2$)$_m$-(benzyl) and —(CH$_2$)$_m$-(substituted benzyl), wherein m is an integer from 1 to about 9;

R2 has the following structural formula:

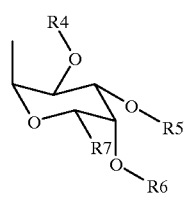

R3 is —CH=C(CH$_3$)$_2$;

R4, R5 and R6 are independently selected from the group consisting of —H and acetyl; and R7 is selected from the group consisting of —H, —CH$_3$ and —CH$_2$OH.

4. The method of claim 1 wherein the compound is selected from the group consisting of pseudopterosin A, pseudopterosin A methyl ether, pseudopterosin C, pseudopterosin C methyl ether, pseudopterosin E and pseudopterosin E methyl ether.

5. A method for reducing the scarring associated with the healing of a wound on an individual or animal comprising contacting the wound with a composition comprising an effective wound healing amount of a compound having the following structural formula:

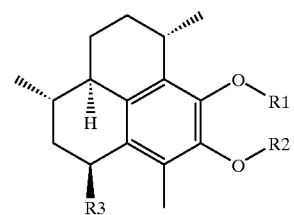

wherein:
R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

6. The method of claim 5 wherein the compound has the following structural formula:

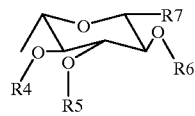

wherein
R1 has the following structural formula:

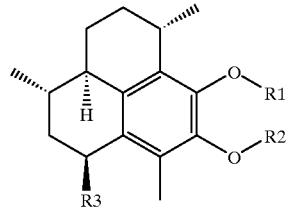

R2 is selected from the group consisting of —H, lower alkyl, benzyl, —(CH$_2$)$_m$—CH$_2$OH, —(CH$_2$)$_m$—CO—NH$_2$, —(CH$_2$)$_m$-(benzyl) and —(CH$_2$)$_m$-(substituted benzyl), wherein m is an integer from 1 to about 9;

R3 is —CH=C(CH$_3$)$_2$;

R4, R5 and R6 are independently selected from the group consisting of —H and acetyl; and R7 is selected from the group consisting of —H, —CH$_3$ and —CH$_2$OH.

7. The method of claim 5 wherein the compound has the following structural formula:

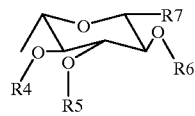

wherein
R1 is selected from the group consisting of —H, lower alkyl, benzyl, —(CH$_2$)$_m$—CH$_2$OH, —(CH$_2$)$_m$—CO—NH$_2$, —(CH$_2$)$_m$-(benzyl) and —(CH$_2$)$_m$-(substituted benzyl), wherein m is an integer from 1 to about 9;

R2 has the following structural formula:

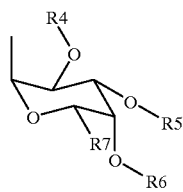

R3 is —CH=C(CH₃)₂;

R4, R5 and R6 are independently selected from the group consisting of —H and acetyl; and R7 is selected from the group consisting of —H, —CH₃ and —CH₂OH.

8. The method of claim 5 wherein the compound is selected from the group consisting of pseudopterosin A, pseudopterosin A methyl ether, pseudopterosin C, pseudopterosin C methyl ether, pseudopterosin E and pseudopterosin E methyl ether.

9. A method of promoting the healing of an internal tissue wound in an individual or animal comprising contacting the wound with a composition comprising an effective wound healing amount of a compound having the following structural formula:

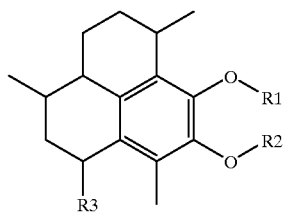

wherein:

R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

10. The method of claim 9 wherein the compound has the following structural formula:

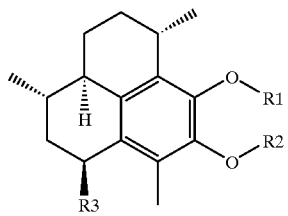

wherein

R1 has the following structural formula:

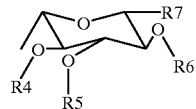

R2 is selected from the group consisting of —H, lower alkyl, benzyl, —(CH₂)ₘ—CH₂OH, —(CH₂)ₘ—CO—NH₂, —(CH₂)ₘ-(benzyl) and —(CH₂)ₘ-(substituted benzyl), wherein m is an integer from 1 to about 9;

R3 is —CH=C(CH₃)₂;

R4, R5 and R6 are independently selected from the group consisting of —H and acetyl; and R7 is selected from the group consisting of —H, —CH₃ and —CH₂OH.

11. The method of claim 9 wherein the compound has the following structural formula:

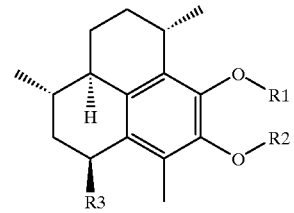

wherein

R1 is selected from the group consisting of —H, lower alkyl, benzyl, —(CH₂)ₘ—CH₂OH, —(CH₂)ₘ—CO—NH₂, —(CH₂)ₘ-(benzyl) and —(CH₂)ₘ-(substituted benzyl), wherein m is an integer from 1 to about 9;

R2 has the following structural formula:

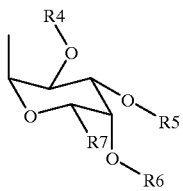

R3 is —CH=C(CH₃)₂;

R4, R5 and R6 are independently selected from the group consisting of —H and acetyl; and R7 is selected from the group consisting of —H, —CH₃ and —CH₂OH.

12. The method of claim 9 wherein the compound is selected from the group consisting of pseudopterosin A, pseudopterosin A methyl ether, pseudopterosin C, pseudopterosin C methyl ether, pseudopterosin E and pseudopterosin E methyl ether.

13. A method of promoting the healing of a wound to dental tissue or eye tissue on an individual or animal comprising contacting the wound with a composition comprising an effective wound healing amount of a compound having the following structural formula:

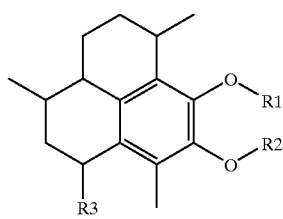

wherein:

R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

14. A method for increasing the adherence of a skin autograft to a wound bed on an individual or animal, comprising applying to the skin autograft an effective wound healing amount of a compound having the following structure formula:

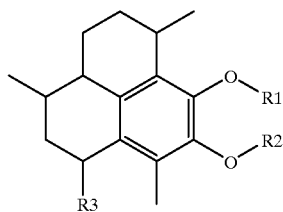

wherein:

R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

15. The method of claim 14 wherein the compound has the following structural formula:

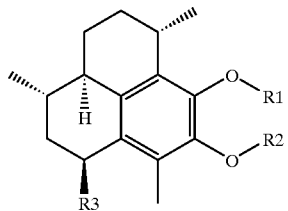

wherein

R1 is selected from the group consisting of —H, lower alkyl, benzyl, —$(CH_2)_m$—$CH_2OH$, —$(CH_2)_m$—$CO$—$NH_2$, —$(CH_2)_m$-(benzyl) and —$(CH_2)_m$-(substituted benzyl), wherein m is an integer from 1 to about 9;

R2 has the following structural formula:

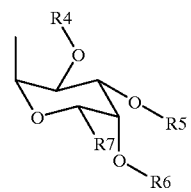

R3 is —$CH$=$C(CH_3)_2$;

R4, R5 and R6 are independently selected from the group consisting of —H and acetyl; and R7 is selected from the group consisting of —H, —$CH_3$ and —$CH_2OH$.

16. A method of promoting the healing of a lesion on the skin of an individual or animal comprising contacting the wound with a composition comprising an effective wound healing amount of a compound having the following structural formula:

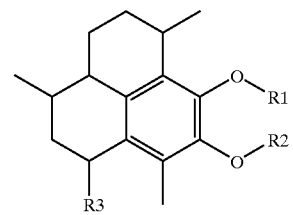

wherein:

R1 and R2 are independently selected from the group consisting of —H, lower alkyl, substituted lower alkyl, phenyl, substituted phenyl, benzyl, substituted benzyl, acyl, alkoxycarbonyl and a monosaccharide and wherein R1 and R2 are different and one of R1 and R2 is a monosaccharide; and R3 is a substituted or unsubstituted lower alkyl group.

17. The method of claim 16 wherein the compound has the following structural formula:

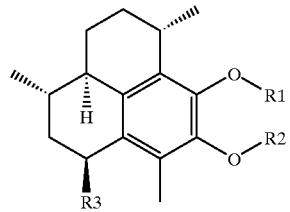

wherein

R1 has the following structural formula:

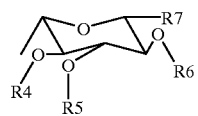

R2 is selected from the group consisting of —H, lower alkyl, benzyl, —$(CH_2)_m$—$CH_2OH$, —$(CH_2)_m$—$CO$—$NH_2$, —$(CH_2)_m$-(benzyl) and —$(CH_2)_m$-(substituted benzyl), wherein m is an integer from 1 to about 9;

R3 is —$CH$=$C(CH_3)_2$;

R4, R5 and R6 are independently selected from the group consisting of —H and acetyl; and R7 is selected from the group consisting of —H, —CH$_3$ and —CH$_2$OH.

18. The method of claim 16 wherein the compound has the following structural formula:

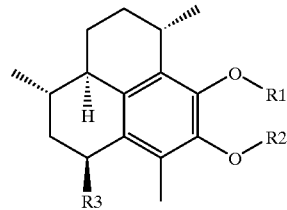

wherein

R1 is selected from the group consisting of —H, lower alkyl, benzyl, —(CH$_2$)$_m$—CH$_2$OH, —(CH$_2$)$_m$—CO—NH$_2$, —(CH$_2$)$_m$-(benzyl) and —(CH$_2$)$_m$-(substituted benzyl), wherein m is an integer from 1 to about 9;

R2 has the following structural formula:

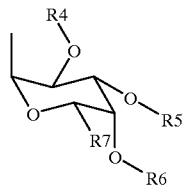

R3 is —CH=C(CH$_3$)$_2$;

R4, R5 and R6 are independently selected from the group consisting of —H and acetyl; and R7 is selected from the group consisting of —H, —CH$_3$ and —CH$_2$OH.

19. The method of claim 16 wherein the compound is selected from the group consisting of pseudopterosin A, pseudopterosin A methyl ether, pseudopterosin C, pseudopterosin C methyl ether, pseudopterosin E and pseudopterosin E methyl ether.

20. A method of promoting the healing of a wound on an individual or animal comprising contacting the wound with a composition comprising an effective wound healing amount of a pseudopterosin or a pseudopterosin derivative.

21. The method of claim 20 wherein the wound is a dermal ulcer, a burn wound or a chemical burn wound, an excisional wound on the skin, an internal tissue wound, a wound to dental tissue or to eye tissue or a partial thickness wound.

22. The method of claim 21 wherein the excisional wound or burn wound extends partially through the epidermis.

23. The method of claim 21 wherein the excisional wound or burn wound extends through at least part of the dermis.

24. The method of claim 20 further comprising reducing the scarring associated with the healing of the wound.

25. A method of promoting the growth and proliferation of keratinocytes, endothelial cells and fibroblasts in a wound on an individual or animal or the re-epithelization of a partial thickness wound on an individual or animal comprising contacting the wound with a composition comprising an effective wound healing amount of a pseudopterosin or a pseudopterosin derivative.

26. A method of increasing the adherence of a skin autograft to a wound bed on an individual or animal comprising applying to the skin autograft an effective wound healing amount of a pseudopterosin or a pseudopterosin derivative.

* * * * *